(12) United States Patent
Bolze et al.

(10) Patent No.: US 12,319,700 B2
(45) Date of Patent: Jun. 3, 2025

(54) MONOHYDRATE POTASSIUM SALT OF A THIENOPYRIDONE DERIVATIVE AND ITS PREPARATION PROCESS

(71) Applicant: POXEL, Lyons (FR)

(72) Inventors: Sébastien Bolze, Massieux (FR); Marc Lanz, Reitnau (CH); Deniz Arican, Lörrach (DE); Anthony O'Sullivan, Basel (CH); Sophie Hallakou-Bozec, Antony (FR); Laure Navarre, Lyons (FR)

(73) Assignee: POXEL, Lyons (FR)

( * ) Notice: Subject to any disclaimer, the term of this patent is extended or adjusted under 35 U.S.C. 154(b) by 838 days.

(21) Appl. No.: 17/293,977

(22) PCT Filed: Nov. 18, 2019

(86) PCT No.: PCT/EP2019/081650
§ 371 (c)(1),
(2) Date: May 14, 2021

(87) PCT Pub. No.: WO2020/099678
PCT Pub. Date: May 22, 2020

(65) Prior Publication Data
US 2022/0017532 A1   Jan. 20, 2022

(30) Foreign Application Priority Data
Nov. 16, 2018 (EP) ...................................... 18306505

(51) Int. Cl.
*C07D 495/04* (2006.01)
(52) U.S. Cl.
CPC .................. *C07D 495/04* (2013.01)

(58) Field of Classification Search
CPC ...................................................... C07D 495/04
USPC .......................................................... 546/114
See application file for complete search history.

(56) References Cited

FOREIGN PATENT DOCUMENTS

WO   WO 2014/001554   1/2014

OTHER PUBLICATIONS

Polymorphism in the Pharmaceutical Industry, 2006, pp. 1-3, edited by Rolf Hilfiker, Wiley-VCH Verlag Gmbh & Co. KGaA, Weinheim, Germany.
Morissette, S.L. et al. "High-throughput crystallization: polymorphs, salts, co-crystals and solvates of pharmaceutical solids" *Advanced Drug Delivery Reviews*, 2004, pp. 275-300, vol. 56.
Crystalline drug, Polymorphic Drugs, Oct. 2009, pp. 1-24, editor-in-chief Yang Lu et al., People's Medical Publishing House, Beijing, China.
Caira, M. R. "Crystalline Polymorphism of Organic Compounds" *Topics in Current Chemistry*, 1998, pp. 163-208, vol. 198.
Wuts, P. G. et al. "Protection for Phenols and Catechols, Protection for Phenols" *Greene's Protective Groups in Organic Synthesis, Fourth Edition*, Apr. 10, 2006, pp. 367-430.
Wuts, P. G. et al. "Protection for the Hydroxyl Group, Including 1,2-and 1,3-Diols" *Greene's Protective Groups in Organic Synthesis, Fourth Edition*, Jan. 1, 2007 pp. 16-366.
Written Opinion in International Application No. PCT/EP2019/081650, Jan. 28, 2020, pp. 1-6.
Byrn, S. et al. "Pharmaceutical Solids: A Strategic Approach to Regulatory Considerations" *Pharmaceutical Research*, Aug. 1995, pp. 945-954, vol. 12, No. 7.
Tian, F. et al. "Factors affecting crystallization of hydrates" *Journal of Pharmacy and Pharmacology*, 2010, pp. 1534-1546, vol. 62.

*Primary Examiner* — Taofiq A Solola
(74) *Attorney, Agent, or Firm* — SALIWANCHIK, LLOYD & EISENSCHENK (57) ABSTRACT

The invention relates to a process for preparing a monohydrate potassium salt of a 5 thienopyridone derivative. It also relates to a monohydrate potassium salt of a thienopyridone derivative and its use in medicine, in particular for treating or preventing metabolic disorders, such as NASH.

18 Claims, 2 Drawing Sheets

MONOHYDRATE POTASSIUM SALT OF A THIENOPYRIDONE DERIVATIVE AND ITS PREPARATION PROCESS

CROSS-REFERENCE TO RELATED APPLICATION

This application is the U.S. national stage application of International Patent Application No. PCT/EP2019/081650, filed Nov. 18, 2019.

TECHNICAL FIELD

The invention relates to a process for preparing a monohydrate potassium salt of a thienopyridone derivative. It also relates to the monohydrate potassium salt of a thienopyridone derivative thus obtained, and its use in medicine, in particular for treating or preventing metabolic disorders, such as NASH.

TECHNICAL BACKGROUND

Adenosine monophosphate-activated protein kinase (AMPK) is a central regulator of multiple metabolic pathways leading to the control of lipid metabolism, glucose homeostasis and inflammation. Its activation has the potential to treat numerous chronic metabolic diseases, including diseases that affect the liver, such as non-alcoholic steatohepatitis (NASH), which is a severe form of non-alcoholic fatty liver disease (NAFLD).

AMPK is an important biological target since it has the potential to trigger benefits on the three key pathophysiology processes involved in NASH development: liver steatosis, inflammation and fibrosis. AMPK activation has the potential to also treat NASH comorbidities, specifically targeting cardiovascular risk factors, such as hyperglycemia, insulin resistance, dyslipidemia, inflammation and obesity.

NASH is a metabolic disease with no clear disease origin that is quickly becoming a worldwide epidemic. It is characterized by hepatic lipid accumulation coming mainly from adipose tissue (AT) lipolysis (60%) and hepatic de novo lipogenesis (25%), causing inflammation and fibrosis. The disease can be silent for a long period of time, but once it accelerates, severe damage and liver cirrhosis can occur, which can significantly impact liver function or can even result in liver failure or liver cancer. Typical risk factors for NASH include obesity, elevated levels of blood lipids (such as cholesterol and triglycerides) and diabetes. Currently no efficient and safe curative or specific therapies are available (G. C. Farrell and C. Z. Larter, Hepatology, 2006, 43, 99-112).

Many thienopyridone derivatives are known to be AMPK activators and have been the subject matter of several applications. In particular, WO 2014/001554 relates to compounds of formula (A):

(A)

wherein R1 is a hydrogen or halogen atom, R2 is an indanyl or tetralinyl group, and R3 is an aryl or heteroaryl group, said compounds being direct activators of AMPK, and also relates to their use in the treatment of disorders regulated by activation of AMPK.

This application also describes a process for preparing the tetrahydrate sodium salt of 2-chloro-4-hydroxy-3-(5-hydroxytetralin-6-yl)-5-phenyl-7H-thieno[2,3-b]pyridin-6-one represented by the following formula (II), comprising mixing the compound of formula (II) with sodium methoxide in methanol and water, and isolating the tetrahydrate sodium salt by lyophilisation.

(II)

The corresponding potassium salt has a great potential due to its pharmacological and physical properties. However, when it is prepared as suggested in WO 2014/001554, according to a process similar to that used for preparing the sodium salt, the compound obtained is amorphous. This process is thus generally more complex to scale up, and requires the use of specific technics like spray drying. Condition adjustments using potassium methoxide in the presence of methanol and water led to an impure methanol solvate. Due to the toxicity of methanol, it is preferable to have access to a hydrate rather than a methanol solvate. Furthermore, substituting the lyophilisation step by a filtration step, which is more appropriate at a larger scale, has proven to provide said impure methanol solvate in low yield.

Thus, there remains a need to develop a process giving access to a stable, well-defined and easy-to-filter potassium salt of compound (II) (2-chloro-4-hydroxy-3-(5-hydroxytetralin-6-yl)-5-phenyl-7H-thieno[2,3-b]pyridin-6-one) with a high yield.

SUMMARY OF THE INVENTION

In this respect, the inventors have demonstrated that a stable, well-defined and easy-to-filter potassium salt of compound (II) can be obtained by modifying the salification step of the process described in WO 2014/001554. The conditions developed by the inventors for this salification step allow access to the monohydrate form of the potassium salt, which has proven to be a stable form. Furthermore, the filtration step gives access to the monohydrate salt in high yield and purity. The inventors have also demonstrated that the precursor, i.e. compound (II), can also be obtained by an efficient process, characterized by the use of greener reagents and mild conditions, an optimized number of steps and a higher overall yield, with respect to the process described in the prior art.

Thus, the invention relates to a process for preparing a monohydrate potassium salt of formula (I):

(I)

said process comprising the steps of:
(A) reacting a compound of formula (II) with potassium carbonate in a solution comprising water and a solvent selected from n-butyl acetate and isopropanol:

(II)

(B) forming a precipitate; and
(C) recovering the precipitate obtained in step (B), preferably by filtration.

It also relates to a monohydrate potassium salt of formula (I):

(I)

This invention further pertains to a pharmaceutical composition comprising a monohydrate potassium salt of formula (I), and a pharmaceutically acceptable support.

It is also directed to the monohydrate potassium salt of formula (I) or the pharmaceutical composition as defined above for use as a medicament, and in particular for use in the treatment or prevention of diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

DETAILED DESCRIPTION OF THE INVENTION

In the following description, the expression "comprised between" is intended to include the upper and lower limits within the range described.

The term "solvent" refers to organic solvent, inorganic solvent such as water, or a mixture thereof. Examples of organic solvents include, but are not limited to, aliphatic hydrocarbons such as pentane or hexane, alicyclic hydrocarbons such as cyclohexane, aromatic hydrocarbons such as benzene, styrene, toluene, ortho-xylene, meta-xylene or para-xylene, halogenated hydrocarbons such as dichloromethane, chloroform or chlorobenzene, nitrogen-based solvents such as acetonitrile or triethylamine, oxygen-based solvents, in particular ketones such as acetone, ethers such as diethyl ether, tert-butyl methyl ether (TBME), cyclopentyl methyl ether (CPME), tetrahydrofuran (THF) or methyl tetrahydrofuran (Me-THF), alcohols such methanol, isopropanol or ethanol, esters such as n-butyl acetate, amides such as dimethylformamide (DMF), and mixtures thereof.

The invention relates to a process for preparing a monohydrate potassium salt of formula (I):

(I)

Said process for preparing a monohydrate potassium salt of formula (I) comprises the steps of:
(A) reacting a compound of formula (II) with potassium carbonate in a solution comprising water and a solvent selected from n-butyl acetate and isopropanol;
(B) forming a precipitate; and
(C) recovering the precipitate obtained in step (B), preferably by filtration.

One or more steps of the process of invention may be divided into substeps.

Potassium carbonate ($K_2CO_3$) in step (A) may be used in the form of a pure solid such as a powder, or may be diluted in a solvent to form a solution or a dispersion. Preferably, potassium carbonate is used in the form of an aqueous solution of potassium carbonate. The concentration of potassium carbonate in said aqueous solution may be comprised between 1% and 99%, preferably between 40% and 60% (w/v). The amount of potassium carbonate used in step (A) may be comprised between 0.25 and 3 equivalents, preferably between 0.5 and 1.2 equivalent, preferably between 0.5 and 0.6 equivalent, relative to the compound of formula (II).

Step (A) may carried out a temperature comprised between 5° C. and 60° C., preferably between 15° C. and 35° C.

In step (A), the compound of formula (II), potassium carbonate, water and a solvent selected from n-butyl acetate and isopropanol, may be added in any suitable reaction vessel or container, and in any order. In one embodiment of the invention, step (A) may be implemented by adding potassium carbonate, in particular an aqueous solution of potassium carbonate, to a solution comprising the compound of formula (II), a solvent selected from n-butyl acetate and isopropanol, and optionally water.

In one particular embodiment, said solvent in step (A) is n-butyl acetate. In such embodiment, step (A) comprises reacting a compound of formula (II) with potassium carbonate in a solution (or "solvent system") comprising water and n-butyl acetate.

When said solvent is n-butyl acetate, the volume ratio of water to n-butyl acetate in step (A) may be comprised between 1/1000 and 100/1, preferably between 1/100 and 10/1, more preferably between 1/100 and 1/2, even more preferably between 1/100 and 1/10.

In another particular embodiment, said solvent in step (A) is isopropanol. In such embodiment, step (A) comprises reacting a compound of formula (II) with potassium carbonate in a solution (or "solvent system") comprising water and isopropanol.

When said solvent is isopropanol, the mass ratio of water to isopropanol in step (A) may be comprised between 25/75 and 75/25, preferably between 40/60 and 60/40, and more preferably between 45/55 and 55/45.

When said solvent is isopropanol, the volume ratio of water to isopropanol in step (A) may be comprised between 20/80 and 70/30, preferably between 35/65 and 55/45, and more preferably between 40/60 and 50/50.

The volume of water refers to the total volume of water in the mixture of step (A), and thus also includes the volume of water which may be brought by an aqueous solution of potassium carbonate.

When said solvent is isopropanol, the mass ratio of compound (II) to the mixture water and isopropanol in step (A) may be comprised between 1/99 and 70/30, preferably between 2/98 and 20/80 more preferably between 5/95 and 15/85.

A mixture comprising the compound of formula (II), potassium carbonate, water and a solvent selected from n-butyl acetate and isopropanol is thus obtained in step (A). Said mixture is advantageously stirred, for instance by action of a magnetic stirrer or an agitation blade.

Step (B) comprises forming a precipitate. Typically, step (B) can comprise a substep of heating the mixture obtained in step (A), preferably at a temperature close to reflux of the mixture, followed by a substep of cooling the resulting mixture, for instance at a temperature comprised between −15° C. and 35° C. The expression "close to reflux of the mixture" refers typically to a temperature comprised between 90% and 100% of the boiling point of the solvent system in step (A) (for instance, water/isopropanol or water/n-butyl acetate).

A distillation step can be carried out between the heating substep and the cooling substep of step (B).

More particularly, step (B) advantageously comprises the following substeps of:
(b1) heating the mixture obtained in step (A) to a temperature comprised between 70° C. and 120° C.; and
(b2) cooling the mixture obtained in step (b1) to a temperature comprised between −15° C. and 35° C., so as to obtain a precipitate.

Steps (b1) and (b2) may independently be divided into one or more temperature gradients, optionally separated by temperature levels. A "temperature level" refers to a phase during which the temperature is maintained constant. A "temperature gradient" refers to a phase during which the temperature increases (in a heating step) or decreases (in a cooling step). Steps (b1) and (b2) may independently end with a temperature gradient or with a temperature level.

It is understood that the temperature of the temperature levels and/or gradients in a given step may be comprised or not within the temperature ranges specified for the final step temperature of the given step. The final step temperature in a given step refers to the highest temperature reached for a heating step and the lowest temperature reached for a cooling step. For instance, the final step temperature in step (b1) is comprised between 70° C. and 120° C., however temperature(s) of the temperature level(s) or gradient(s) in step (b1) may be comprised or not within the range 70-120° C.

Step (b1) comprises heating said mixture obtained in step (A) to a temperature $T_{b1}$ comprised between 70° C. and 120° C., preferably between 90° C. and 110° C. or between 80° C. and 100° C. Said temperature $T_{b1}$ may be maintained for 5 minutes to 10 hours, preferably for 10 minutes to 10 hours, more preferably for 15 minutes to 5 hours, even more preferably for 20 minutes to 2 hours. The source for heating may be any suitable device known to the skilled artisan.

In one particular embodiment, step (b1) comprises the following substeps:
(b1-1) heating the mixture obtained in step (A) to a temperature $T_3$ comprised between 45° C. and 60° C., $T_3$ being maintained for 30 minutes to 10 hours, preferably 1 hour to hours; and
(b1-2) heating the mixture obtained in step (b1-1) to a temperature $T_{b1}$ comprised between 70° C. and 90° C., preferably between 75° C. and 85° C., $T_{b1}$ being maintained for 5 minutes to 2 hours, preferably for 5 minutes to 30 minutes.

In such embodiment, said solvent selected from n-butyl acetate and isopropanol is advantageously isopropanol.

Step (b2) comprises cooling the mixture obtained in step (b1) to a temperature comprised between −15° C. and 35° C.

In one embodiment, step (b2) comprises the following substeps:
(b2-1) cooling the mixture obtained in step (b1) to a temperature $T_1$ comprised between 13° C. and 35° C. over a period $P_1$ comprised between 30 minutes and 5 hours, preferably between 45 minutes and 2 hours;
(b2-2) cooling the mixture obtained in step (b2-1) to a temperature $T_2$ comprised between −5° C. and 10° C., preferably between 0° C. and 5° C., over a period $P_2$ comprised between 10 minutes and 5 hours, preferably between 45 minutes and 2 hours; and
(b2-3) maintaining said temperature $T_2$ for 45 minutes to 250 minutes.

In this embodiment, rates $r_1=(T_{b1}-T_1)/P_1$ and $r_2=(T_1-T_2)/P_2$ may be different.

In such embodiment, said solvent selected from n-butyl acetate and isopropanol is advantageously n-butyl acetate.

Substep (b2-1) above may be followed, before substep (b2-2), by a temperature level at the temperature $T_1$, for 15 minutes to 10 hours, preferably for 30 minutes to 3 hours.

In another embodiment, step (b2) comprises the following substeps:
- (b2-1') cooling the mixture obtained in step (b1) to a temperature $T_{1'}$ comprised between 30° C. and 50° C. over a period $P_{1'}$ comprised between 60 minutes and 6 hours, preferably between 90 minutes and 2 hours;
- (b2-2') cooling the mixture obtained in step (b2-1') to a temperature $T_{2'}$ comprised between −5° C. and 10° C., preferably between 0° C. and 10° C., over a period $P_{2'}$ comprised between 1 hour and 20 hours, preferably between 45 minutes and 2 hours; and
- (b2-3') maintaining said temperature $T_{2'}$ for 1 hour to 15 hours.

In this embodiment, rates $r_{1'}=(T_{b1}-T_{1'})/P_{1'}$ and $r_{2'}=(T_{1'}-T_{2'})/P_{2'}$ may be different.

In such embodiment, said solvent selected from n-butyl acetate and isopropanol is advantageously isopropanol.

A filtration, such as a polish filtration, may be carried out between steps (b1) and (b2).

In a preferred embodiment, said solvent selected from n-butyl acetate and isopropanol is isopropanol, and said step (B) further comprises a distillation step. The distillation step aims at removing a part of the solvents of the solvent system. Preferably, the distillation step is carried out between steps (b1) and (b2), or simultaneously with step (b2), for instance between step (b2-1') and step (b2-2').

Said distillation step is preferably carried out under a reduced pressure. The reduced pressure to apply depends on the temperature at the distillation step, and can be easily determined by the skilled artisan. For instance, the temperature of the distillation step may be comprised between 20° C. and 120° C., preferably between 30° C. and 90° C., and the reduced pressure may be comprised between 1 mbar and 500 mbar, preferably between 10 mbar and 300 mbar.

Water is advantageously added to the reaction mixture prior to and/or after carrying out the distillation step.

In a particular embodiment, said solvent selected from n-butyl acetate and isopropanol is isopropanol, and the mass ratio of isopropanol to water is equal to or less than 15/85, preferably equal to or less than 10/90 at the end of the distillation step.

Step (B) allows a precipitate to form. Said precipitate is crystalline. Seeds may be added in step (b2), preferably early in step (b2), such as in steps (b2-1), (b2-2), (b2-1'), or (b2-2'). More generally, early in step (b2) may be within the first 60 minutes of step (b2), preferably the first 30 minutes of step (b2), more preferably the first 15 minutes of step (b2), the origin of step (b2) being the time at which the temperature of the mixture obtained in step (b1) starts decreasing.

"Seeds" refers to crystals, which are typically added in small amounts to a mixture in order to favor or trigger the formation of a crystalline precipitate. In step (B) of the process according to the invention, said seeds are advantageously composed of the monohydrate potassium salt of formula (I).

The precipitate obtained in step (B) comprises crystalline particles of monohydrate potassium salt of formula (I). In one embodiment, at least 50 wt % of the monohydrate potassium salt of formula (I) obtained in step (B) is in the form of crystalline particles having a particle size higher than or equal to 10 μm. Alternatively or in addition, at least 20 wt % of the monohydrate potassium salt of formula (I) obtained in step (B) is in the form of crystalline particles having a particle size higher than or equal to 35 μm.

Step (C) of the process according to the invention comprises recovering the precipitate obtained in step (B). In one preferred embodiment, said precipitate is recovered by filtration. Filtration may be carried out with a filter having a pore size between 10 and 50 μm, preferably between and 40 μm. The precipitate recovered in step (C) by filtration comprises crystalline particles of monohydrate potassium salt of formula (I), which particle size is higher than or equal to the pore size of the filter. In a particular embodiment, the precipitate recovered in step (C) by filtration comprises crystalline particles of monohydrate potassium salt of formula (I) having a particle size of at least 10 μm, preferably at least 25 μm.

The precipitate may be washed successively with one or more solvents, preferably water, n-butyl acetate and/or tert-butyl methyl ether.

Said precipitate is mostly composed of the monohydrate potassium salt of formula (I). The purity of said precipitate, i.e. the purity of the monohydrate potassium salt of formula (I) obtained by the process according to the invention is advantageously above 98% a/a, preferably above 99% a/a, as measured by high performance liquid chromatography (HPLC) or any other suitable technique known to the skilled artisan.

The compound of formula (II) and a preparation process thereof have been disclosed in patent application WO 2014/001554.

Alternatively, said compound of formula (II) may be obtained by an improved process comprising the steps of:
- (a') reacting 6-acetyl-5-hydroxytetralin with an electrophilic benzyl source in the presence of a base $B_1$;
- (b') reacting the compound obtained in step (a') with ethyl cyanoacetate in the presence of hexamethyldisilazane and acetic acid;
- (c') reacting the compound obtained in step (b') with sulfur in the presence of a base $B_2$;
- (d') optionally forming a salt of the compound obtained in step (c'), preferably a hydrochloride salt;
- (e') reacting the compound obtained in step (c') or (d') with N-chlorosuccinimide;
- (f') reacting the compound obtained in step (e') with phenylacetyl chloride;
- (g') reacting the compound obtained in step (f') with a base $B_3$;
- (h') reacting the compound obtained in step (g') with boron tribromide or trichloride, preferably boron trichloride; and
- (i') optionally recovering the compound obtained in step (h').

Conditions (such as temperature, concentration, equivalents of the reactants, reaction solvents, or work-up solvents) for each step from (a') to (i') are described below for particular and/or preferred embodiments, and may be adjusted by the skilled artisan using his/her general background. Each step reaction may be treated, and each intermediate or product obtained from a step reaction may be isolated, and optionally purified, for instance by seeded or unseeded crystallization, recrystallization or chromatography. Alternatively, several steps may be carried out in one-pot without treating said reaction and/or isolating said reaction intermediate or reaction product. One or more of these steps may be divided into substeps. The "treatment" of a reaction refers to the use of reagents such as an acid or a base, and/or solvents, to stop the reaction, and typically to eliminate all or part of reaction impurities by extraction techniques and washing(s). The "purification" refers to the use of one or more techniques such as crystallization or chromatography, aiming at improving the purity (i.e. eliminating further reaction impurities) and/or the crystallinity of the reaction product.

Step (a') comprises protecting the hydroxy group of 6-acetyl-5-hydroxytetralin. In patent application WO 2014/001554, a methyl group is chosen as protecting group, which is inserted by using methyl iodide. In the present invention, the hydroxy group of 6-acetyl-5-hydroxytetralin is protected with a benzyl group, which may be inserted by using electrophilic benzyl sources which are less toxic and less volatile than methyl iodide.

An "electrophilic benzyl source" refers to a chemical reagent which is able, in the presence or not of a activating agent such as a catalyst, to release or to transfer an electrophilic benzyl group, i.e. formally "Ph-CH$_2$$^+$", to another compound. Examples of electrophilic benzyl sources include, but are not limited to benzyl halides, such as benzyl bromide or benzyl iodide, benzyl triflate and benzyl 2,2,2-trichloroacetimidate. Preferably, said electrophilic benzyl source is benzyl bromide. The amount of said electrophilic benzyl source in step (a') may be comprised between 1 and 5 equivalents, preferably between 1 and 2 equivalents, more preferably between 1 and 1.2 equivalent, relative to 6-acetyl-5-hydroxytetralin.

Step (a') is advantageously carried out in the presence of a base $B_1$. $B_1$ may be a hydroxide source such as potassium hydroxide or sodium hydroxide, potassium carbonate, cesium carbonate, a nitrogen-based base such as triethylamine or morpholine, or a mixture thereof. The amount of $B_1$ in step (a') may be comprised between 1 and 5 equivalents, preferably between 1 and 2 equivalents, more preferably between 1 and 1.2 equivalent, relative to 6-acetyl-5-hydroxytetralin.

In one particular embodiment, step (a') is carried out in a biphasic solvent system comprising dichloromethane and water, in the presence of a phase transfer agent such as tetrabutylammonium bromide. In this embodiment, $B_1$ is advantageously a hydroxide source such as potassium or sodium hydroxide. In this embodiment, step (a') is advantageously carried out at a temperature comprised between 5° C. and 50° C., preferably between 15° C. and 35° C.

In a preferred embodiment, step (a') is carried out in a monophasic solvent system, such as in acetonitrile or acetone, preferably acetonitrile. In this preferred embodiment, $B_1$ is advantageously potassium carbonate or cesium carbonate, preferably potassium carbonate. In this preferred embodiment, step (a') is advantageously carried out at a temperature comprised between 40° C. and 100° C., preferably between 60° C. and 90° C.

The compound obtained in step (a'), i.e. the O-benzylated 6-acetyl-5-hydroxytetralin, may be reacted in step (b') with ethyl cyanoacetate in the presence of hexamethyldisilazane (HMDS) and acetic acid. The amount of ethyl cyanoacetate and HMDS in step (b') may be, independently from each other, comprised between 1 and 5 equivalents, preferably between 1.1 and 2 equivalents, relative to the compound obtained in step (a'). Acetic acid may be used in excess and may be used as a reagent and solvent. Step (b') is advantageously carried out at a temperature comprised between 30° C. and 100° C., preferably between 50° C. and 90° C.

Treatment of the reaction in step (b') may be carried out by means of a binary solvent system comprising a basic aqueous solution, such as a $Na_2CO_3$, $NaHCO_3$ or NaOH aqueous solution, and an organic solvent, such as tert-butyl methyl ether (TBME), ethyl acetate, iso-propyl acetate, or a mixture thereof. A preferred basic aqueous solution and a preferred organic solvent for said treatment are respectively a NaOH aqueous solution and TBME.

In a particular embodiment, the compound obtained in step (b'), i.e. ethyl 3-(5-benzyloxytetralin-6-yl)-2-cyano-but-2-enoate, is not isolated after said treatment, and is directly subjected to a reaction with sulfur $S_8$ in step (c').

The amount of sulfur in step (c') may be comprised between 1 and 5 atom equivalents, preferably between 1 and 2.5 atom equivalents, more preferably between 1 and 1.1 atom equivalent, relative to the compound obtained in step (b').

1 atom equivalent of sulfur $S_8$ is ⅛ equivalent of sulfur $S_8$.

Step (c') is advantageously carried out in the presence of a base $B_2$. $B_2$ may be a hydroxide source such as potassium hydroxide or sodium hydroxide, sodium carbonate, potassium carbonate, cesium carbonate, sodium hydrogenocarbonate, a nitrogen-based base such as triethylamine or morpholine, or a mixture thereof. $B_2$ is preferably sodium hydrogenocarbonate or morpholine, and more preferably $B_2$ is sodium hydrogenocarbonate. The amount of $B_2$ in step (c') may be comprised between 1 and 5 equivalents, preferably between 1 and 2 equivalents, relative to the compound obtained in step (b'). Step (c') may be carried out in any organic solvent, preferably in ethanol or a mixture ethanol/TBME, more preferably in a mixture ethanol/TBME.

Step (c') is advantageously carried out at a temperature comprised between 40° C. and 100° C., preferably between 50° C. and 90° C.

In a particular embodiment, the compound obtained in step (c'), i.e. ethyl 2-amino-4-(5-benzyloxytetralin-6-yl)thiophene-3-carboxylate, is reacted in step (d') with an acid to form the corresponding salt. Said acid is a Brønsted acid such as hydrochloric acid, hydrobromic acid, hydroiodic acid, sulfuric acid, nitric acid, phosphoric acid, formic acid, acetic acid, trifluoroacetic acid, methanesulfonic acid, benzenesulfonic acid or p-toluenesulfonic acid. Preferably, said acid is hydrochloric acid. Said acid may be in the form of a pure gas, liquid or solid, or may be solubilized in a solvent such as dioxane. Step (d') may be carried out in any organic solvent, such as ethanol, TBME, ethyl acetate or a mixture thereof. Step (d') is advantageously carried out at a temperature comprised between 5° C. and 100° C., preferably between 15° C. and 35° C.

Said salt formed in step (d') may precipitate and thus be isolated by filtration. A recrystallization of the salt obtained in step (d') may be carried out by using an organic solvent, selected from an ester such as ethyl acetate or n-butyl acetate, toluene or an ether such methyl tetrahydrofuran, cyclopentyl methyl ether, preferably ethyl acetate.

The compound obtained in step (c') or the corresponding salt of acid from step (d') may be subjected in step (e') to a chlorination by reacting with an electrophilic chlorine source. An "electrophilic chlorine source" refers to a chemical reagent which is able, in the presence or not of an activating agent such as a catalyst, to release or to transfer an electrophilic chlorine group, i.e. formally "Cl*", to another compound. Examples of electrophilic chlorine source include, but are not limited to, N-chlorosuccinimide (NCS) or N-chlorophthalimide. Preferably, said electrophilic chlorine source is NCS. The amount of electrophilic chlorine source in step (e') may be comprised between 1 and 5 equivalents, preferably between 1 and 2 equivalents, more preferably between 1 and 1.1 equivalent relative to the compound obtained in step (c') or (d'). Step (e') may be carried out in any organic solvent, such as dichloromethane or chloroform, preferably in dichloromethane. The temperature in step (e') is advantageously comprised between −30° C. and 25° C., preferably between −5° C. and 10° C., more preferably between 0° C. and 5° C. A base such as sodium or potassium carbonate, or sodium or potassium hydrogenocarbonate, preferably potassium carbonate, may be used in step (e'), in particular when step (e') is carried out with the compound obtained in step (d').

In a preferred embodiment, steps (e') and (f') are carried out successively without isolating the compound obtained in step (e').

In step (f'), the compound obtained in step (e'), i.e. ethyl 2-amino-4-(5-benzyloxytetralin-6-yl)-5-chloro-thiophene-3-carboxylate, or a salt of acid thereof, may be reacted with phenyacetyl chloride. The amount of phenylacetyl chloride in step (f') may be comprised between 1 and 5 equivalents, preferably between 1 and 2 equivalents, more preferably between 1 and 1.5 equivalent relative to the compound obtained in step (e').

The temperature in step (f') is advantageously comprised between −30° C. and 25° C., preferably between −5° C. and 25° C., more preferably between 0° C. and 5° C.

Step (f') is advantageously carried out in the same solvent as step (e'). The compound obtained in step (f'), i.e. ethyl 4-(5-benzyloxytetralin-6-yl)-5-chloro-2-[(2-phenylacetyl) amino]-thiophene-3-carboxylate, may be crystallized and/or recrystallized in an organic solvent such as acetone, ethanol, TBME, methanol, ethanol, or a mixture thereof, preferably ethanol.

Step (g') comprises reacting the compound obtained in step (f') with a base $B_3$, which triggers a cyclisation reaction.

Step (g') may be carried out in any organic solvent, such as THF, methyl tetrahydrofuran, or toluene, preferably in THF or methyl tetrahydrofuran. Said base $B_3$ may be selected from the group consisting of sodium or potassium amide, sodium or potassium hydride, sodium or potassium bis(trimethylsilyl)amide, sodium or potassium tert-butoxide, and sodium or potassium tert-pentoxide, preferably $B_3$ is potassium tert-butoxide or potassium bis(trimethylsilyl)amide, more preferably $B_3$ is potassium tert-butoxide. The amount of $B_3$ in step (g') may be comprised between 2 and 10 equivalents, preferably between 2.5 and 6 equivalents, more preferably between 4 and 6 equivalents relative to the compound obtained in step (f'). The reaction in step (g') is advantageously carried out under an inert atmosphere, such as under nitrogen or argon atmosphere.

In one particular embodiment, step (g') is carried out at a temperature comprised between −40° C. and 15° C., preferably between −30° C. and 10° C., typically upon addition of $B_3$ to the mixture comprising the compound obtained in step (f'), and then at a temperature comprised between 15° C. and 40° C.

The compound obtained in step (g'), i.e. 3-(5-benzyloxytetralin-6-yl)-2-chloro-4-hydroxy-5-phenyl-7H-thieno [2,3-b]pyridin-6-one, may be crystallized in an organic solvent such as heptane, TBME, isopropyl acetate, or a mixture thereof.

The protecting group (i.e. the benzyl group) inserted in step (a') can be removed in step (h') by reacting the compound obtained in step (g') with a suitable deprotection reagent. Said deprotection reagent may be boron tribromide, boron trichloride, or hydrobromic acid. In a particular embodiment, said deprotection reagent is hydrobromic acid, in combination with acetic acid. In this particular embodiment, hydrobromic acid may be used in the form of a solution in acetic acid or water. In this particular embodiment, the reaction may be carried out in acetic acid, and optionally acetic anhydride. In a preferred embodiment, said deprotection reagent is boron tribromide or boron trichloride. In a more preferred embodiment, said deprotection reagent is boron trichloride. Boron tribromide or boron trichloride may be used in the form of a pure gas, or diluted in an organic solvent such as dichloromethane. The amount of deprotection reagent in step (h') may be comprised between 1 and 10 equivalents, preferably between 1 and 5 equivalents, more preferably between 1 and 2.5 equivalents relative to the compound obtained in step (g'). Step (h') may be carried out in any organic solvent, preferably dichloromethane.

In one particular embodiment, step (h') is carried out at a temperature comprised between −40° C. and 15° C., preferably between −20° C. and 10° C., upon addition of the deprotection reagent to the mixture comprising the compound obtained in step (g'), and then at a temperature comprised between 15° C. and 40° C.

The compound obtained in step (h'), i.e. the compound of formula (II), namely 2-chloro-4-hydroxy-3-(5-hydroxytetralin-6-yl)-5-phenyl-7H-thieno[2,3-b]pyridin-6-one may be crystallized and/or recrystallized in any organic solvent such as heptane, dichloromethane, methanol, toluene, or a mixture thereof, preferably a mixture of methanol and toluene.

The compound obtained in step (h') may be recovered, for instance by filtration after crystallization and/or recrystallization. The compound obtained in step (h') may be used as a precursor for preparing the monohydrate potassium salt of formula (I) according to the process of the invention.

In patent application WO 2014/001554, the methyl group, used as protecting group, is removed by means of methanesulfonic acid. The reaction generates methyl methanesulfonate, which is known to be genotoxic. In the present invention, the use of a benzyl as protecting group, which can be removed with a boron tribromide or trichloride, or hydrobromic acid, avoids the formation of such a genotoxic impurity.

The monohydrate potassium salt of formula (I) may be obtained from compound (II) according to the process of the invention with a yield higher than or equal to 85%, preferably higher than or equal to 90%. In a particular embodiment, compound (II) used as starting material in the process of the invention may be obtained from 6-acetyl-5-hydroxytetralin with a yield higher than or equal to 30%, preferably higher than or equal to 40%, more preferably higher than or equal to 50%.

The present invention also relates to a monohydrate potassium salt of the compound of formula (II). Said monohydrate potassium salt may be represented by the following formula (I):

(I)

Said monohydrate potassium salt is advantageously in the form of crystalline particles. In one embodiment, at least 50 wt % of said monohydrate potassium salt is in the form of crystalline particles of 10 μm or more. Alternatively or in addition, at least 20 wt % of said monohydrate potassium salt is in the form of crystalline particles of 35 μm or more. Said crystalline particles may have any form and may particularly exist as crystalline conglomerates.

Said monohydrate potassium salt may be in the form of a solid, such as a powder, having the following XRPD (X-Ray Powder Diffraction) peaks, as measured by means of a diffractometer, using Cu K (alpha) radiation:

| 2-theta (°) | d-value (Å) |
|---|---|
| 4.910 | 17.9826 |
| 11.560 | 7.6486 |
| 13.010 | 6.7992 |
| 14.720 | 6.0130 |
| 16.450 | 5.3843 |
| 17.330 | 5.1128 |
| 17.770 | 4.9872 |
| 18.690 | 4.7437 |
| 19.220 | 4.6141 |
| 19.640 | 4.5164 |
| 20.190 | 4.3946 |
| 21.170 | 4.1933 |
| 21.580 | 4.1145 |
| 22.190 | 4.0028 |
| 22.700 | 3.9140 |
| 23.240 | 3.8243 |
| 23.860 | 3.7263 |
| 24.410 | 3.6435 |
| 25.330 | 3.5133 |
| 26.230 | 3.3947 |
| 26.730 | 3.3323 |
| 28.700 | 3.1079 |
| 29.590 | 3.0164 |
| 29.950 | 2.9810 |
| 30.960 | 2.8860 |
| 31.570 | 2.8316 |
| 32.200 | 2.7776 |
| 33.080 | 2.7057 |
| 33.530 | 2.6704 |
| 34.050 | 2.6308 |
| 34.750 | 2.5794 |
| 35.530 | 2.5246 |
| 35.950 | 2.4960 |
| 36.660 | 2.4493 |
| 37.300 | 2.4087 |
| 38.320 | 2.3469 |
| 39.490 | 2.2801 |

In particular, said monohydrate potassium salt may be in the form of a solid, such as a powder, having the following XRPD (X-Ray Powder Diffraction) peaks, as measured by means of a diffractometer, using Cu K (alpha) radiation:

| 2-theta (°) | d-value (Å) | Intensity* |
|---|---|---|
| 4.910 | 17.9826 | weak |
| 11.560 | 7.6486 | weak |
| 13.010 | 6.7992 | medium |
| 14.720 | 6.0130 | strong |
| 16.450 | 5.3843 | weak |
| 17.330 | 5.1128 | medium-strong |
| 17.770 | 4.9872 | weak |
| 18.690 | 4.7437 | weak |
| 19.220 | 4.6141 | weak |
| 19.640 | 4.5164 | medium |
| 20.190 | 4.3946 | weak |
| 21.170 | 4.1933 | medium |
| 21.580 | 4.1145 | weak |
| 22.190 | 4.0028 | weak |
| 22.700 | 3.9140 | medium |
| 23.240 | 3.8243 | weak |
| 23.860 | 3.7263 | medium |
| 24.410 | 3.6435 | medium-strong |
| 25.330 | 3.5133 | weak |
| 26.230 | 3.3947 | weak |
| 26.730 | 3.3323 | medium |
| 28.700 | 3.1079 | medium |
| 29.590 | 3.0164 | weak |
| 29.950 | 2.9810 | weak |
| 30.960 | 2.8860 | medium-strong |
| 31.570 | 2.8316 | weak |
| 32.200 | 2.7776 | weak |
| 33.080 | 2.7057 | weak |
| 33.530 | 2.6704 | weak |
| 34.050 | 2.6308 | weak |
| 34.750 | 2.5794 | medium |
| 35.530 | 2.5246 | medium-strong |
| 35.950 | 2.4960 | medium |
| 36.660 | 2.4493 | medium |
| 37.300 | 2.4087 | weak |
| 38.320 | 2.3469 | weak |
| 39.490 | 2.2801 | weak |

*strong > medium-strong > medium > weak

Preferably, said monohydrate potassium salt may be in the form of a solid, such as a powder, having the following XRPD (X-Ray Powder Diffraction) peaks, as measured by means of a diffractometer, using Cu K (alpha) radiation:

| 2-theta (°) | d-value (Å) | Intensity* |
|---|---|---|
| 13.010 | 6.7992 | medium |
| 14.720 | 6.0130 | strong |
| 17.330 | 5.1128 | medium-strong |
| 19.640 | 4.5164 | medium |
| 21.170 | 4.1933 | medium |
| 22.700 | 3.9140 | medium |
| 23.860 | 3.7263 | medium |
| 24.410 | 3.6435 | medium-strong |
| 26.730 | 3.3323 | medium |
| 28.700 | 3.1079 | medium |
| 30.960 | 2.8860 | medium-strong |
| 34.750 | 2.5794 | medium |
| 35.530 | 2.5246 | medium-strong |
| 35.950 | 2.4960 | medium |
| 36.660 | 2.4493 | medium |

*strong > medium-strong > medium

More preferably, said monohydrate potassium salt may be in the form of a solid, such as a powder, having the following XRPD (X-Ray Powder Diffraction) peaks, as measured by means of a diffractometer, using Cu K (alpha) radiation:

| 2-theta (°) | d-value (Å) |
|---|---|
| 13.010 | 6.7992 |
| 14.720 | 6.0130 |
| 17.330 | 5.1128 |
| 19.640 | 4.5164 |
| 21.170 | 4.1933 |
| 22.700 | 3.9140 |
| 23.860 | 3.7263 |
| 24.410 | 3.6435 |
| 26.730 | 3.3323 |
| 28.700 | 3.1079 |
| 30.960 | 2.8860 |

-continued

| 2-theta (°) | d-value (Å) |
|---|---|
| 34.750 | 2.5794 |
| 35.530 | 2.5246 |
| 35.950 | 2.4960 |
| 36.660 | 2.4493 |

The present invention furthermore relates to a pharmaceutical composition comprising the monohydrate potassium salt according to the invention and a pharmaceutically acceptable support.

The present invention also relates to a monohydrate potassium salt of the invention or a pharmaceutical composition according to the invention for use as a medicament.

In particular, the present invention relates to a monohydrate potassium salt of the invention or a pharmaceutical composition according to the invention for use in the treatment of a subject, in particular in the treatment of diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

In a preferred embodiment, a monohydrate potassium salt of the invention or a pharmaceutical composition according to the invention are for use in the treatment of diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies or neuropathies.

In a more preferred embodiment, a monohydrate potassium salt of the invention or a pharmaceutical composition according to the invention are for use in the treatment of diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia or hypercholesterolemia. In an even more preferred embodiment, the monohydrate potassium salt of the invention is for use in the treatment of NAFLD or NASH.

The term "cancer" in the present invention includes cancers with solid or liquid tumors. In particular, it refers to glioblastomas, neuroblastomas, leukemias, prostate cancers, ovarian cancers, lung cancers, breast cancers, digestive cancers, in particular liver cancers, pancreatic cancers, head and neck cancers, colon cancers, lymphomas and melanomas.

A further object of this invention is a method for treating diseases regulated by activation of AMPK, more specifically diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases, the method comprising administering to a subject in need thereof an effective amount of a monohydrate potassium salt of the invention or a pharmaceutical composition of the invention.

The invention furthermore relates to the use of a monohydrate potassium salt of the invention for the preparation of a pharmaceutical composition, in particular for the treatment of diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

The pharmaceutical composition according to the invention may be prepared by any conventional method. A monohydrate potassium salt of the invention can be converted into a suitable dosage form here together with at least one solid, liquid and/or semi-liquid excipient or adjuvant and, if desired, in combination with one or more further active ingredients.

The term "pharmaceutically acceptable support" refers to carrier, adjuvant, or excipient acceptable to the subject from a pharmacological/toxicological point of view and to the manufacturing pharmaceutical chemist from a physical/chemical point of view regarding to composition, formulation, stability, subject acceptance and bioavailability.

The term "carrier", "adjuvant", or "excipient" refers to any substance, not itself a therapeutic agent, that is added to a pharmaceutical composition to be used as a carrier, adjuvant, and/or diluent for the delivery of a therapeutic agent to a subject in order to improve its handling or storage properties or to enable or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc.

The term "treatment" or "treating" refers to therapy, prevention and prophylaxis of a disorder which can be potentially regulated by activation of AMPK, in particular diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

The treatment involves the administration of a monohydrate potassium salt of the invention or a pharmaceutical composition of the invention to a subject having a declared disorder to cure, delay, or slow down the progress, thus improving the condition of patients. The treatment may be also administered to healthy subjects that are at risk of developing a disorder, in particular diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

Within the context of the invention, the term "subject" means a mammal and more particularly a human. The subjects to be treated according to the invention can be appropriately selected on the basis of several criteria associated to the disease such as previous drug treatments, associated pathologies, genotype, exposure to risk factors, viral infection, as well as any other relevant biomarker that can be evaluated by means of immunological, biochemical, enzymatic, chemical, or nucleic acid detection method. In a particular embodiment, the subject is an overweighed patient (in particular an overweighed prediabetic patient) or obese patient suffering from atherogenic dyslipidemia. Indeed, these patients are at risk of developing a disease which can be potentially regulated by activation of AMPK, in particular diabetes, metabolic syndrome, obesity, liver disease, hepatic steatosis, non-alcoholic fatty liver disease (NAFLD), non-alcoholic steato-hepatitis (NASH), liver fibrosis, dyslipidemia, hypertriglyceridemia, hypercholesterolemia, inflammation, cancer, cardiovascular diseases, atherosclerosis, high blood pressure, retinopathies, neuropathies, mitochondrial disorders and myopathies, including but not limited to, MELAS (mitochondrial encephalomyopathy, lactic acidosis, and stroke-like episodes), Leigh Syndrome, LHON (Leber's hereditary optic neuropathy), or MNGIE (Mitochondrial neurogastrointestinal encephalomyopathy), neuromuscular diseases such as Duchenne Muscular Dystrophy, Becker Muscular Dystrophy (BMD), or Spinal Muscular Dystrophy, neurodegenerative diseases, pulmonary fibrosis, age-associated neurological diseases, Alzheimer disease, or metabolic diseases.

Pharmaceutical compositions can be administered in the form of dosage units which comprise a predetermined amount of active ingredient per dosage unit. Such a unit can comprise, for example, 0.5 mg to 1000 mg, preferably 20 mg to 1000 mg, more preferably 60 mg to 500 mg, of a monohydrate potassium salt according to the invention, depending on the disease condition treated, the method of administration and the age, weight and condition of the patient, or pharmaceutical compositions can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical compositions of this type can be prepared using a process which is generally known in the pharmaceutical art.

The ratio between a monohydrate potassium salt of the invention and the pharmaceutically acceptable support may be comprised in a wide range. In particular, this ratio may be comprised between 5/95 (w/w) and 90/10 (w/w), preferably between 10/90 (w/w) and 80/20 (w/w).

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such compositions can be prepared using all processes known in the pharmaceutical art by, for example, combining the active ingredient with the excipient(s) or adjuvant(s). Preferably, the pharmaceutical composition according to the invention is adapted for oral administration.

Pharmaceutical compositions adapted for oral administration can be administered as separate units, such as, for example, capsules or tablets; powders or granules; solutions or suspensions in aqueous or non-aqueous liquids; edible foams or foam foods; or emulsions, such as oil-in-water liquid emulsions or water-in-oil liquid emulsions.

Thus, for example, in the case of oral administration in the form of a tablet or capsule, the active ingredient component can be combined with an oral, non-toxic and pharmaceutically acceptable inert excipient. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules may be produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compound according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Pharmaceutical compositions adapted for oral administration can also be formulated by spray drying of a solid or liquid dispersion.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The monohydrate potassium salt according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

A therapeutically effective amount of a monohydrate potassium salt of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. It can be assumed that similar doses are suitable for the treatment of other conditions mentioned above.

The invention will also be described in further detail in the following examples, which are not intended to limit the scope of this invention, as defined by the attached claims.

EXAMPLES

Abbreviations eq.: equivalent
a/a: ratio of the peak area of a given compound to the total of the peak areas on a spectrum or a chromatogram.
Analytical Methods
XRPD X-Ray Powder Diffraction (XRPD) analyses were performed using a Panalytical Xpert Pro diffractometer equipped with a Cu (K alpha radiation) X-ray tube and a Pixcel detector system. The samples were analyzed in transmission mode and held between low density polyethylene, Kapton® and/or polypropylene films. XRPD patterns were sorted, manipulated and indexed using HighScore Plus 2.2c software.

Kapton® exhibits a broad peak with a low intensity around 2Theta=5.5°.

The intensity of XRD peaks depends on the light interference of the radiation dispersed for the group of atoms forming the "base" of the crystal structure, and/or on the crystals orientation.
TG/DTA Thermogravimetric (TG) analyses were carried out on a Perkin Elmer Diamond Thermogravimetric/Differential Temperature Analyser (TG/DTA). The calibration standards were indium and tin. Samples were placed in an aluminium sample pan, inserted into the TG furnace and accurately weighed. The samples were heated from 30-300° C. in a stream of nitrogen at a rate of 10° C./minute. The temperature of the furnace was equilibrated at 30° C. prior to the analysis of the samples.

Example 1: Synthesis of the Monohydrate Potassium Salt of Formula (I)

1a) Synthesis of 1-(5-benzyloxytetralin-6-yl)ethanone (1)

(1)

6-Acetyl-5-hydroxytetralin (100 g, 1 eq.) was dissolved in acetonitrile (300 mL). After addition of K$_2$CO$_3$ (1.1 eq.) and benzyl bromide (1.05 eq.), the suspension was heated (76° C.). After 48 hours, benzyl bromide (0.1 eq) was added. After overall 74 hours, the solid was filtered off and washed with acetonitrile (200 mL), and the combined filtrates were evaporated.

Compound 1 was obtained as a syrup: m=148.6 g, quantitative yield, 96.6% a/a purity.

1b) Synthesis of ethyl 2-amino-4-(5-benzyloxytetralin-6-yl)thiophene-3-carboxylate (2)

(2)

Acetic acid (70 mL) was heated to T=65° C. HMDS (1.5 eq.) was added over 10 min. Afterwards, a solution of compound 1 (69.5 g, 1 eq.) and ethyl cyanoacetate (1.5 eq.) in acetic acid (140 mL) was added. The resulting mixture was stirred at T=65° C. for 24 h.

After cooling to room temperature, aqueous NaOH (1 M, 140 mL) and TBME (210 mL) were added. The layers were separated. The organic layer was washed with aqueous NaOH (1 M, 4×140 mL) until the pH of the aqueous phase was basic (pH=13). The organic layer was washed with aqueous HCl (1M, 140 mL) and H$_2$O (2×140 mL).

EtOH (240 mL), NaHCO$_3$ (1.3 eq.) and sulfur (1.0 atom eq.) were added. After heating to reflux for 180 min, the reaction mixture was concentrated to 210 mL and co-evaporated with TBME (3×140 mL). After cooling to room temperature, the suspension was filtered and the solid was washed with TBME (70 mL). The combined filtrates were concentrated to 210 mL and HCl in dioxane (1.1 eq.) was added dropwise at room temperature. After seeding, precipitation was observed. Heptane (350 mL) was added dropwise at room temperature. After stirring for 14 h, the suspension was filtered. After washing with heptane (3×70 mL) and drying, compound 2 was recovered as a solid. m=83.2 g, 71% yield, 93.7% a/a purity.

1c) Synthesis of ethyl 4-(5-benzyloxytetralin-6-yl)-5-chloro-2-[(2-phenylacetyl)amino]thiophene-3-carboxylate (3)

(3)

Compound 2 (17.69 g, 1 eq.) was dissolved in dichloromethane (140 mL). The resulting solution was cooled with ice/water. Under stirring, N-chlorosuccinimide (1.05 eq.) was added. The mixture became dark over a few minutes. After 1 h, phenylacetyl chloride (1.25 eq.) was added.

After 1 hour at 0° C. and 2 hours at room temperature, the mixture was evaporated down to ca. 35 mL and EtOH (2×70 mL) was added, and evaporated down again. The mixture was diluted with EtOH (35 mL) and cooled with ice/water. The product precipitated. The solid was filtrated and washed with cold EtOH (3×18 mL).

Compound 3 was obtained as a solid: m=20.99 g, 94.2% yield, 99.3% a/a purity.

1d) Synthesis of 3-(5-benyloxytetralin-6-yl)-2-chloro-4-hydroxy-5-phenyl-7H-thieno[2,3-b]pyridin-6-one (4)

(4)

Compound 3 (19.88 g, 1 eq.) was solubilized in methyltetrahydrofuran (120 mL), and the reaction mixture was cooled to a temperature between −16° C. and −10° C. (NaCl/Ice). Potassium tert-butoxide (5 eq.) was added in four portions. Then, the reaction mixture was warmed up to room temperature, and stirred for 65 min at room temperature. A dropwise addition of 2N HCl (5 eq.) was carried out at T=0-5° C. (water/ice) and the resulting mixture was stirred vigorously. The organic phase was washed with NaCl$_{(aq)}$ (11%, 1×50 mL) and water (2×50 mL). The organic phase was concentrated to ~50% solution. Methyltetrahydrofuran (80 mL) was added, and the resulting solution was concentrated to ~50% solution. TBME (100 mL) was added, and the resulting solution was concentrated to ~50% solution (this step was repeated 3 times). Then, TBME (25 mL), seeds of compound 4 and n-Heptane (20 mL) were added and the resulting solution was stirred at room temperature overnight. The mixture was concentrated to ca. 50 mL, filtrated, rinsed with mother liquor and washed with n-Heptane (2×40 mL) and dried. Compound 4 was obtained as a granular solid. Yield 88%, 99.5% a/a purity.

1e) Synthesis of 2-chloro-4-hydroxy-3-(5-hydroxytetralin-6-yl)-5-phenyl-7H-thieno[2,3-b]pyridin-6-one (I)

(II)

Compound 4 (15 g, 1 eq.) was dissolved in 75 mL of dichloromethane and was cooled to T=−10° C./−15° C. (with ice/NaCl). BCl$_3$ (1.5 eq., solution: 1 mol/L in dichloromethane) was added dropwise and the resulting mixture was stirred at room temperature for 15 hours. The resulting mixture was cooled with ice/water, and water (75 mL) was added. The resulting mixture was stirred vigorously and the organic phase was extracted with water/MeOH (9:1 v/v, 5×45 mL.). The organic phase was concentrated, a solvent swap was carried out with toluene (3×90 mL) and diluted with toluene to reach a final volume of 90 mL of toluene. The resulting mixture was heated to reflux and 15 mL of methanol was added. A brownish solution with few particles was obtained. Seeds were added at T=40° C., warmed to T=52° C. and cooled to room temperature. The resulting mixture was stirred overnight, and then was cooled with ice/NaCl (T=−10° C./−15° C.) for 100 minutes. The precipitated product was filtrated, washed with toluene/heptane 1:2 v/v (15 mL) and heptane (15 mL) and dried. Crystals of compound (II) were obtained: 87% yield, 99.0% a/a purity.

1f) Synthesis of the monohydrate potassium salt of 2-chloro-4-hydroxy-3-(S-hydroxytetralin-6-yl)-5-phenyl-7H-thieno[2,3-b]pyridin-6-one (I). using n-butyl acetate (I)

Compound (II) (8.43 g) was stirred with n-butyl acetate (42 mL). Water and K$_2$CO$_3$ (50% aq; 0.55 eq.) were added. Altogether, 3 mL water including that from K$_2$CO$_3$ solution was added. No change in appearance was observed. The resulting mixture was heated at 100° C. After 35 minutes at that temperature, the heating was stopped, seeds were added, and stirring continued. The mixture was left to slowly cool to room temperature. After 60 minutes, the mixture was cooled with ice-water to T=0-5° C. for 125 minutes. The solid was then filtered off and washed with n-butyl acetate (10 mL), then TBME (2×35 mL) and dried.

Compound (I) was obtained as a white solid: m=8.44 g, 90% yield, 99.3% a/a purity.

1f') Synthesis of the monohydrate potassium salt of 2-chloro-4-hydroxy-3-(5-hydroxytetralin-6-yl)-5-phenyl-7H-thieno[2,3-b]pyridin-6-one (I), using isopropanol Compound (II) was suspended in water/isopropanol mix (1/1, 5 parts of each solvents) then 0.50 to 0.55 eq of potassium carbonate was added. The pH was about 12 (pH indicator paper) at the end of the addition of potassium carbonate. After 3 hours of stirring at 50° C., the suspension was thicker and the pH was about 8 (pH indicator paper). The temperature was raised to 80° C. until a solution was obtained (10-15 minutes). A clarification can be done at this point of the process if required. 7 parts of water were added and the reaction mixture was then cooled to 40° C. (turbid solution observed). The solvent was distilled under reduce pressure (from 180 mbar to 40 mbar) at 40° C. until 7 parts of solvents remained in the reactor. Crystallization of potassium salt monohydrate may occur here. 4.2 parts of water were added and the mixture was seeded with compound (I) (1 to 2% of seeds). The suspension was then cooled down from 40° C. to 5° C. in 7 hours (5° C./hour) and kept at 5° C. for several hours. The suspension was filtered. The cake was washed twice by 1.42 parts of water. The collected solid was dried at 40° C. under vacuum given minimum 80% yield of Compound (I), at required chemical purity (i.e. 98%+).

Example 2: Characterization of Compound (I)

a) X-ray powder diffraction (XRPD) data of compound (I) indicated that it was composed of a crystalline material. The XRPD description of compound (I) is shown in Table 1 (see also FIG. 1).

TABLE 1

Figure 1:
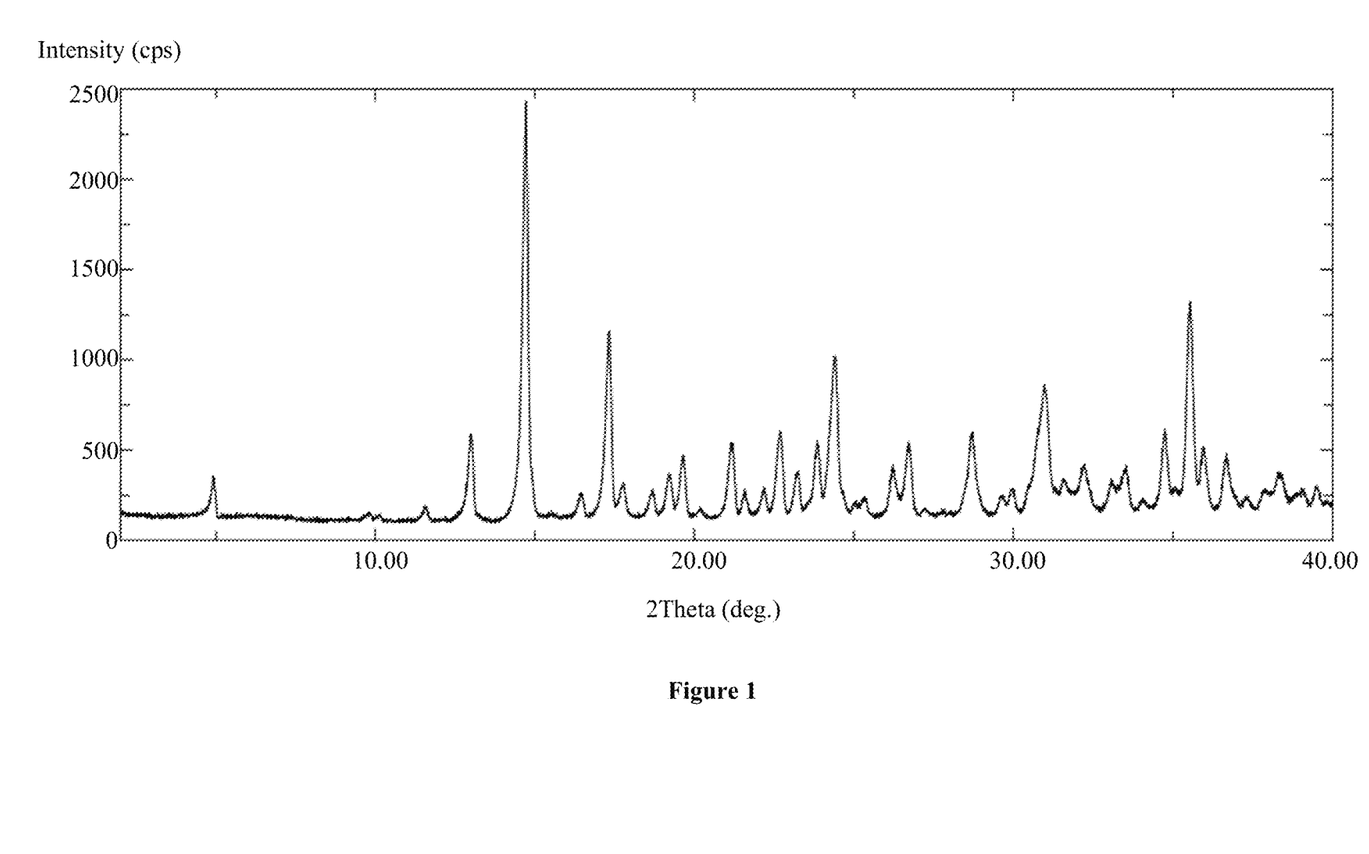
FIG. 1 shows the XRPD pattern of compound (I) as prepared in Example 1.

| Peak No | 2-theta (°) | d-value (Å) | Relative intensity (%) |
|---|---|---|---|
| 1 | 4.910 | 17.9826 | 15 |
| 2 | 11.560 | 7.6486 | 8 |
| 3 | 13.010 | 6.7992 | 25 |
| 4 | 14.720 | 6.0130 | 100 |
| 5 | 16.450 | 5.3843 | 11 |
| 6 | 17.330 | 5.1128 | 49 |
| 7 | 17.770 | 4.9872 | 14 |
| 8 | 18.690 | 4.7437 | 12 |
| 9 | 19.220 | 4.6141 | 16 |
| 10 | 19.640 | 4.5164 | 20 |
| 11 | 20.190 | 4.3946 | 8 |
| 12 | 21.170 | 4.1933 | 23 |
| 13 | 21.580 | 4.1145 | 12 |
| 14 | 22.190 | 4.0028 | 12 |
| 15 | 22.700 | 3.9140 | 26 |
| 16 | 23.240 | 3.8243 | 17 |
| 17 | 23.860 | 3.7263 | 23 |

TABLE 1-continued

| Peak No | 2-theta (°) | d-value (Å) | Relative intensity (%) |
|---|---|---|---|
| 18 | 24.410 | 3.6435 | 43 |
| 19 | 25.330 | 3.5133 | 10 |
| 20 | 26.230 | 3.3947 | 17 |
| 21 | 26.730 | 3.3323 | 23 |
| 22 | 28.700 | 3.1079 | 25 |
| 23 | 29.590 | 3.0164 | 11 |
| 24 | 29.950 | 2.9810 | 13 |
| 25 | 30.960 | 2.8860 | 36 |
| 26 | 31.570 | 2.8316 | 15 |
| 27 | 32.200 | 2.7776 | 18 |
| 28 | 33.080 | 2.7057 | 14 |
| 29 | 33.530 | 2.6704 | 17 |
| 30 | 34.050 | 2.6308 | 10 |
| 31 | 34.750 | 2.5794 | 26 |
| 32 | 35.530 | 2.5246 | 56 |
| 33 | 35.950 | 2.4960 | 22 |
| 34 | 36.660 | 2.4493 | 20 |
| 35 | 37.300 | 2.4087 | 11 |
| 36 | 38.320 | 2.3469 | 16 |
| 37 | 39.490 | 2.2801 | 13 | b) TG/DTA analysis showed an initial weight loss of 1.1% from 30-100° C., followed by larger weight loss of 3% from 117-160° C. due to loss of bound water. The second weight loss was accompanied by a large endotherm and the combined weight losses of 4% approximate the theoretical weight loss for a monohydrate (3.75% w/w). The compound decomposed above 240° C.

Example 3: Comparative Study

3a) Formation of a Potassium Salt of Compound (II) According to WO 2014/001554

Figure 2:
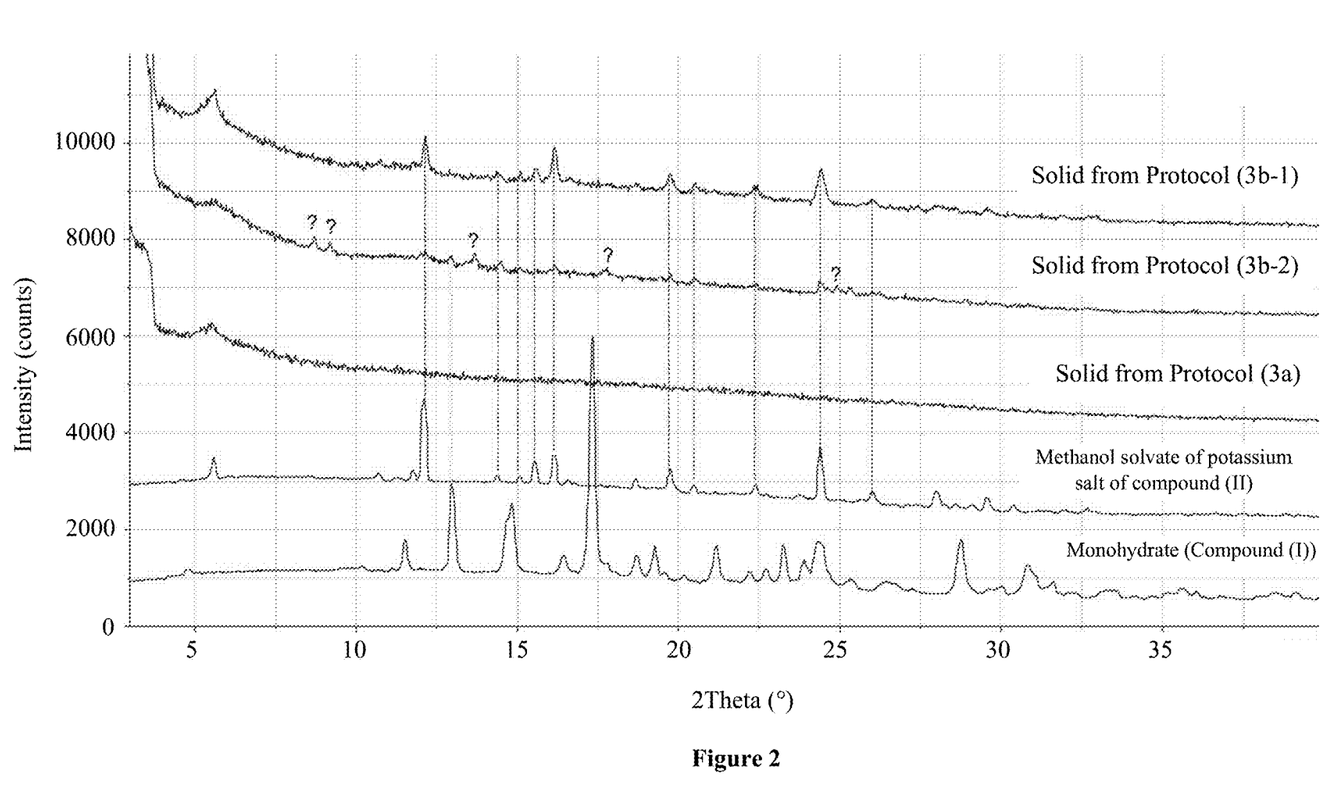
FIG. 2 shows XRPD patterns of solids obtained from various protocols, a XRPD pattern of the methanol solvate of the potassium salt of compound (II), and a XRPD pattern of compound (I).

Compound (II) (1 g) was suspended in MeOH (6.25 mL)/THF (6.25 mL). Potassium methoxide MeOK (1.0 eq.) was added followed by water (3.75 mL). The resulting mixture was evaporated to dryness A lyophilization step was then carried out. However, XRPD analysis demonstrated that an amorphous solid was obtained (FIG. 2—Protocol 3a).

3b) Formation of a Potassium Salt of Compound (II) Using MeOH/MeOK Under Various Conditions 1) Compound (II) (1 g) was suspended in MeOH (12.5 mL). Potassium methoxide MeOK (1.0 eq.) was added followed by water (7.5 mL) and the mixture was heated to T=50° C. for 20 minutes. The reaction was stopped when pH reached ca. 10. The resulting mixture was cooled to room temperature and evaporated to dryness. The mixture was slowly cooled to room temperature and then, a lyophilization step was then carried out. However, XRPD analysis demonstrated that an impure methanol solvate was obtained (FIG. 2—Protocol 3b-1).
2) The lyophilization step described above (3b-1) was replaced by a filtration step. However, a low filtration yield was obtained (starting from 1 g of compound II: 57 mg of solid obtained after filtration), and XRPD analysis demonstrated that the product was an impure methanol solvate (FIG. 2—Protocol 3b-2).

In the absence of water in protocols 3b-1 or 3b-2, a methanol solvate was obtained.

Example 4: Pharmaceutical Compositions

Table 2 shows 20% drug loading blends, 250 g batch scale formula used to manufacture 30 mg strength capsules.

TABLE 2

| Component | % in blend | Quantity (g) | Quantity per capsule (30 mg strength) (mg) |
|---|---|---|---|
| Intra-granular | | | |
| Compound (I)* | 20.00 | 50.000 | 33.96 |
| Lactose monohydrate | 46.00 | 115.000 | 78.11 |
| Microcrystalline cellulose | 23.00 | 57.500 | 39.05 |
| Crospovidone | 5.00 | 12.500 | 8.49 |
| Povidone | 3.00 | 7.500 | 5.09 |
| Sodium lauryl sulfate | 2.00 | 5.000 | 3.40 |
| Extra-granular | | | |
| Silicon dioxide | 0.25 | 0.625 | 0.42 |
| Magnesium Stearate | 0.75 | 1.875 | 1.27 |
| Total | 100.00% | 250.000 | 169.8 |

*A salt correction factor of 1.132 has been used (with respect to the neutral non-hydrated compound (II)) to account for the monohydrate potassium salt.

Table 3 shows 75% drug loading blends, 250 g batch scale formula used to manufacture 125 mg and 250 mg strength capsules.

TABLE 3

| | | | Quantity per capsule (mg) | |
|---|---|---|---|---|
| Component | % in blend | Quantity (g) | 125 mg strength | 250 mg strength |
| Intra-granular | | | | |
| Compound (I)* | 75.00 | 187.500 | 141.50 | 283.00 |
| Lactose monohydrate | 8.00 | 20.000 | 15.09 | 30.19 |
| Microcrystalline cellulose | 4.00 | 10.000 | 7.55 | 15.09 |
| Crospovidone | 5.00 | 12.500 | 9.43 | 18.87 |
| Povidone | 5.00 | 12.500 | 9.43 | 18.87 |
| Sodium lauryl sulfate | 2.00 | 5.000 | 3.77 | 7.55 |
| Extra-granular | | | | |
| Silicon dioxide | 0.25 | 0.625 | 0.47 | 0.94 |
| Magnesium Stearate | 0.75 | 1.875 | 1.42 | 2.83 |
| Total | 100.00% | 250.000 | 188.7 | 377.3 |

*A salt correction factor of 1.132 has been used (with respect to the neutral non-hydrated compound (II)) to account for the monohydrate potassium salt.

Example 5: Biological Tests

The effects of the monohydrate potassium salt of formula (I) (or "Compound (I)") on liver and adipose tissue (AT) metabolism in a diet-induced obesity non-alcoholic steatohepatitis (DIO-NASH) mouse model are reported here.

After 41 weeks, only DIO-NASH mice with biopsy-confirmed steatosis (score ≥2) and fibrosis (stage ≥1) were included and received orally (n=12) vehicle (ctrl), compound (I) 35 or 75 mg/kg twice daily for 8 weeks.

Compared to normal chow diet mice, DIO-NASH mice exhibited characteristics of NASH including steatohepatitis (NAFLD Activity Score, NAS=7), liver fibrosis (score=2), elevated liver triglycerides (TG, x26) as well as liver inflammation. As expected, compound (I) at both doses increased AMPK activity in the liver (P-AMPK/AMPK, +128%; +143%, p<0.05) and improved liver health. Compared to ctrl group, compound (I) at both doses decreased liver weight (−23%, p<0.01; −33%, p<0.01). Compound (I) reduced NAS (−32% (from 6.6 to 4.5); −44% (from 6.7 to 3.8), p<0.01) decreasing steatosis, also confirmed by the reduction of liver TG content (−36%; −42%, p<0.01), inflammation and hepatocellular ballooning. The benefit of the compound (I) on fibrosis was measured by a strong down-regulation in the expression of fibrotic genes (e.g. type I collagen, −65%; −68%, p<0.01) and a decrease in hepatic stellate cell activation (aSMA positive staining −34%; −39%, p<0.01).

In addition to the benefits on the liver, compound (I) improved adipose tissue metabolism. Compound (I) activated AMPK (P-AMPK/AMPK, +130% ns; +152%, p<0.01) in visceral AT and reduced fat pad mass (−25%; −37%, p<0.01). Compound (I) decreased the activity of hormone-sensitive lipase (P-HSLser565+416%; +425%, p<0.01, P-HSLser563 −67%; −52%), consistent with the decrease in plasma free fatty acid level (−37%; −38%, p<0.01). Compound (I) reduced AT inflammation, decreasing MCP-1 gene expression (−55% p<0.05 at 75 mg/kg) and increased AT mitochondrial biogenesis, increasing PGCl-α protein expression (+321%; +409%, p<0.01).

Conclusion: Compound (I) evidenced beneficial effects on NAFLD/NASH, liver fibrosis and inflammation acting on both liver and adipose tissue in DIO-NASH mice model through direct activation of AMPK.

The effects of the monohydrate potassium salt of formula (I) (or "Compound (I)") on dyslipidemia in a model of dyslipidemia are reported here.

Effects of Compound (I) in male obese diabetic dyslipidemic ob/ob mice after 5 weeks of treatment.

Compound (I) was administered at 25, 50 and 100 mg/kg twice a day by oral route in carboxy methylcellulose 0.5%/Tween 80 (98/2) (n=10). A group of ob/ob mice was treated with carboxy methylcellulose 0.5%/Tween 80 (98/2) as a control group.

Compared to normal normal ob/+ mice, ob/ob mice exhibited dyslipidemia.

After 5 weeks of treatment with Compound (I), a decrease of plasma triglyceride (−19% NS, −40% p<0.001 and −43% p<0.001 respectively at 25 mg/kg, 50 mg/kg and 100 mg/kg), plasma FFA (−14% NS, −35% p<0.05 and −21% NS respectively) and an increase in HDL cholesterol (+12% NS, +31% p<0.001 and +32% p<0.001 respectively at 25 mg/kg, 50 mg/kg and 100 mg/kg) were observed.

Conclusion: Compound (I) thus evidenced beneficial effects on dyslipidemia.

The effects of the monohydrate potassium salt of formula (I) (or "Compound (I)") on body weight gain in an obese model are reported here.

Effects of Compound (I) in male obese diabetic dyslipidemic ob/ob mice after 5 weeks of treatment.

Compound (I) was administered at 25, 50 and 100 mg/kg twice a day by oral route in carboxy methylcellulose 0.5%/Tween 80 (98/2) (n=10). A group of ob/ob mice was treated with carboxy methylcellulose 0.5%/Tween 80 (98/2) as a control group.

Compared to normal normal ob/+ mice, ob/ob mice exhibited obesity with an increase in body weight gain.

After 5 weeks of treatment with Compound (I), a decrease of body weight compared to day 1 (−17%, −24%, −113% respectively at 25 mg/kg, 50 mg/kg and 100 mg/kg) was observed.

Conclusion: Compound (I) thus evidenced beneficial effects on obesity, more particularly by decreasing body weight gain.

The effects of the monohydrate potassium salt of formula (I) (or "Compound (I)") on arterial pressure in conscious unrestrained rat model of hypertension are reported here.

The effects of Compound (I) on arterial pressure was measured in conscious unrestrained well-known rat model of hypertension, the Spontaneous Hypertensive Rat (SHR), using telemetry. SHR aged of 21-22 weeks present a higher arterial pressure compared to healthy Wistar rats: systolic arterial pressure was 200 mmHg vs 120 mmHg in Wistar rats.

Four male SHR were submitted to surgery to implant a blood pressure catheter into the abdominal aorta. The telemetry transmitter was attached to the peritoneum. Ten days after recovery, the same animal received vehicle or Compound (I) 150 mg/kg bid administered for 5 days, 5 weeks apart. Systolic, diastolic and mean arterial pressures were recorded during 24 h, the $5^{th}$ day of treatment.

Compound (I) 150 mg/kg bid administered for 5 days in SHR reduced systolic arterial pressure (SAP), −19 mmHg, diastolic arterial pressure (DAP), −17 mmHg and mean arterial pressure (DAP), −18 mmHg, over 24 h, compared to vehicle-treated SHR.

Conclusion: Compound (I) thus allows to decrease high blood pressure in a rat model of hypertension. Compound (I) thus evidenced beneficial effects on hypertension.

The invention claimed is:
1. A process for preparing a monohydrate potassium salt of formula (I):

said process comprising the steps of:
(A) reacting a compound of formula (II) with potassium carbonate in a solution comprising water and a solvent selected from n-butyl acetate and isopropanol:

(B) forming a precipitate; and
(C) recovering the precipitate obtained in step (B).

2. The process according to claim 1, wherein step (B) comprises the following substeps of:
   (b1) heating the mixture obtained in step (A) to a temperature comprised between 70° C. and 120° C.; and
   (b2) cooling the mixture obtained in step (b1) to a temperature comprised between −15° C. and 35° C., so as to obtain a precipitate.

3. The process according to claim 1, wherein said solvent is isopropanol.

4. The process according to claim 1, wherein the amount of potassium carbonate used in step (a) is between 0.25 and 3 equivalents relative to said compound of formula (II).

5. The process according to claim 4, wherein the amount of potassium carbonate used in step (a) is between 0.5 and 0.6 equivalent.

6. The process according to claim 1, wherein the precipitate is recovered by filtration.

7. The process according to claim 1, wherein said compound of formula (II) is obtained by a process comprising the steps of:
   (a') reacting 6-acetyl-5-hydroxytetralin with an electrophilic benzyl source in the presence of a first base ($B_1$);
   (b') reacting the compound obtained in step (a') with ethyl cyanoacetate in the presence of hexamethyldisilazane and acetic acid;
   (c') reacting the compound obtained in step (b') with sulfur in the presence of a second base ($B_2$);
   (d') optionally forming a salt of the compound obtained in step (c');
   (e') reacting the compound obtained in step (c') or (d') with an electrophilic chlorine source;
   (f') reacting the compound obtained in step (e') with phenylacetyl chloride;
   (g') reacting the compound obtained in step (f') with a third base ($B_3$);
   (h') reacting the compound obtained in step (g') with boron tribromide or trichloride; and
   (i') optionally recovering the compound obtained in step (h').

8. The process according to claim 7, wherein step (a') is carried out in acetonitrile and $B_1$ is potassium carbonate.

9. The process according to claim 7, wherein in step (c') $B_2$ is morpholine or sodium hydrogenocarbonate.

10. The process according to claim 7, wherein $B_3$ in step (g') is potassium bis(trimethylsilyl)amide or potassium tert-butoxide.

11. The process according to claim 10, wherein $B_3$ is potassium tert-butoxide.

12. The process according to claim 7, wherein the electrophilic chlorine source is N-chlorosuccinimide.

13. The process according to claim 7, wherein the compound obtained in step (g') with boron trichloride.

14. The process according to claim 7, wherein the salt, when formed, is a hydrochloride salt.

15. A monohydrate potassium salt of formula (I):

(I)

16. The monohydrate potassium salt according to claim 15, which is in the form of a solid having the following XRPD peaks, as measured by means of a diffractometer, using Cu K(alpha) radiation:

| 2-theta (°) | d-value (Å) |
| --- | --- |
| 13.010 | 6.7992 |
| 14.720 | 6.0130 |
| 17.330 | 5.1128 |
| 19.640 | 4.5164 |
| 21.170 | 4.1933 |
| 22.700 | 3.9140 |
| 23.860 | 3.7263 |
| 24.410 | 3.6435 |
| 26.730 | 3.3323 |
| 28.700 | 3.1079 |
| 30.960 | 2.8860 |
| 34.750 | 2.5794 |
| 35.530 | 2.5246 |
| 35.950 | 2.4960 |
| 36.660 | 2.4493. |

17. The process according to claim 7, wherein 6-acetyl-5-hydroxytetralin is reacted with benzyl bromide in step (a') in the presence of $B_1$.

18. The process according to claim 17, wherein 6-acetyl-5-hydroxytetralin is reacted with benzyl bromide in acetonitrile in the presence of potassium carbonate ($B_1$).

* * * * *